United States Patent [19]

Pigneul et al.

[11] Patent Number: 4,617,022
[45] Date of Patent: Oct. 14, 1986

[54] DISPOSABLE HYGIENIC ARTICLE WITH REMOVABLE BELT

[75] Inventors: Raymond Pigneul, Durrenentzen; Dominique Pannier; Benoit Tresca, both of Colmar, all of France

[73] Assignee: Beghin-Say S.A., Thumeries, France

[21] Appl. No.: 784,689

[22] PCT Filed: Jan. 25, 1985

[86] PCT No.: PCT/FR85/00014
  § 371 Date: Sep. 25, 1985
  § 102(e) Date: Sep. 25, 1985

[87] PCT Pub. No.: WO85/03205
  PCT Pub. Date: Aug. 1, 1985

[30] Foreign Application Priority Data

Jan. 27, 1984 [FR] France .................. 84 01333
May 18, 1984 [FR] France .................. 84 07713
Nov. 6, 1984 [FR] France .................. 84 16844

[51] Int. Cl.⁴ .................................. A61F 13/16
[52] U.S. Cl. .................................. 604/391; 604/394
[58] Field of Search ............... 604/387, 389, 390, 391, 604/394, 385

[56] References Cited

U.S. PATENT DOCUMENTS

| 2,509,674 | 5/1950 | Cohen | 604/391 |
| 2,695,025 | 11/1954 | Andrews | 604/391 |
| 2,931,747 | 4/1960 | Dexter | 604/389 X |
| 3,089,494 | 5/1963 | Schwartz | 604/391 |
| 3,150,664 | 9/1964 | Noel | 604/391 |
| 3,869,761 | 3/1975 | Schaar | 604/390 |
| 4,186,744 | 2/1980 | Ness | 604/390 |

FOREIGN PATENT DOCUMENTS 1435900 2/1969 Fed. Rep. of Germany.
2112863 6/1972 France.

Primary Examiner—John D. Yasko
Attorney, Agent, or Firm—A. W. Breiner

[57] ABSTRACT

The invention concerns the field of hygiene and relates to a disposable article (1) combined removably with a removable belt (12), the attachment of one to the other being obtained by means of "Velcro"® attachment elements.

The article comprises a first attachment element (11) fixed near each longitudinal edge on the external face of a trunk area (4); the means of attachment combined removably consist of a belt (12) provided at each extremity with a complementary second attachment element (16) of the first attachment element (11), and the other external trunk area (4) and/or at least one area (13) of the belt coming into contact with this external trunk area has a coefficient of friction sufficient to maintain the article in position by the combination of the first attachment elements (11) by means of the belt provided with the complementary second attachment elements (16).

22 Claims, 9 Drawing Figures

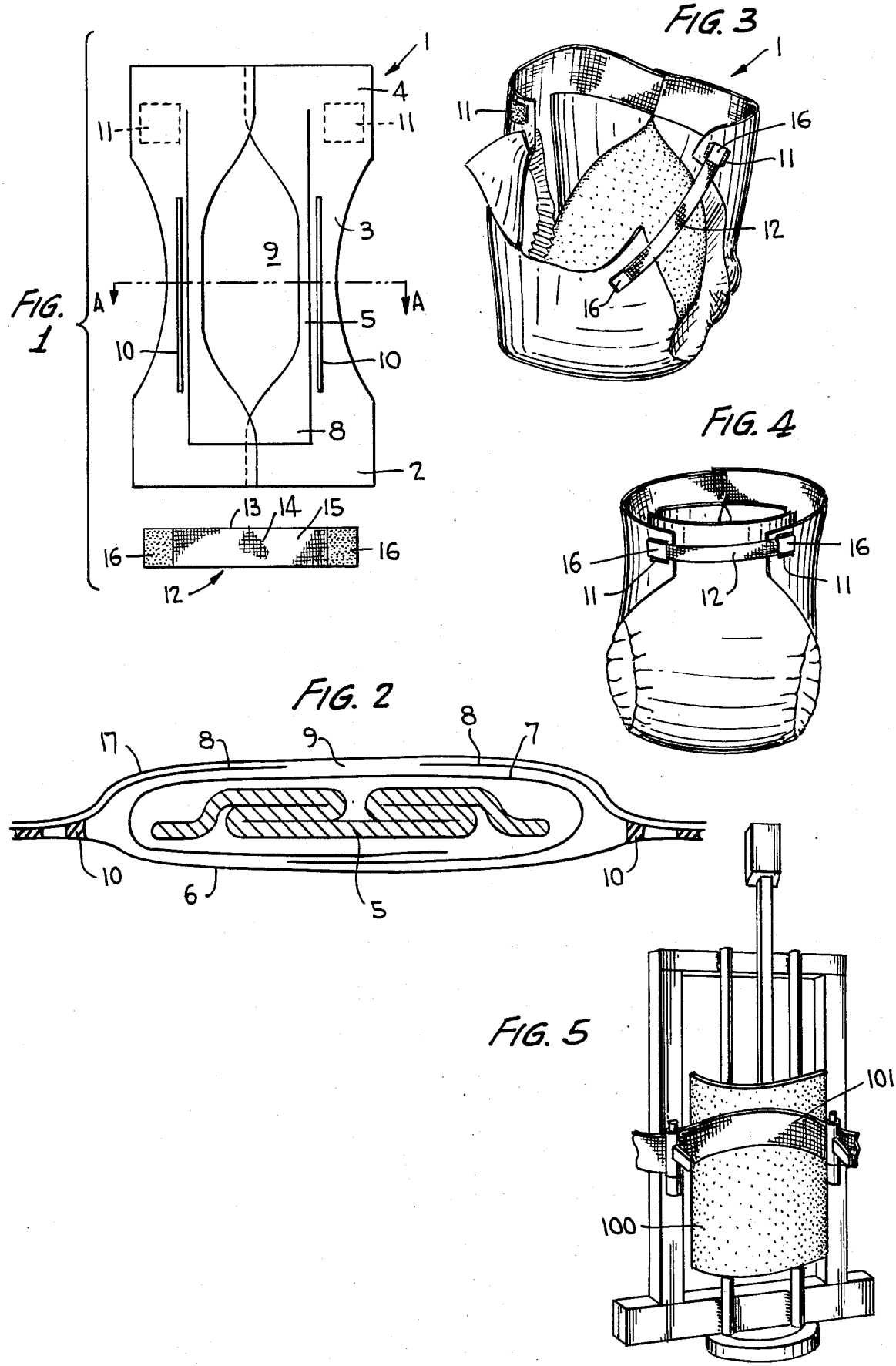

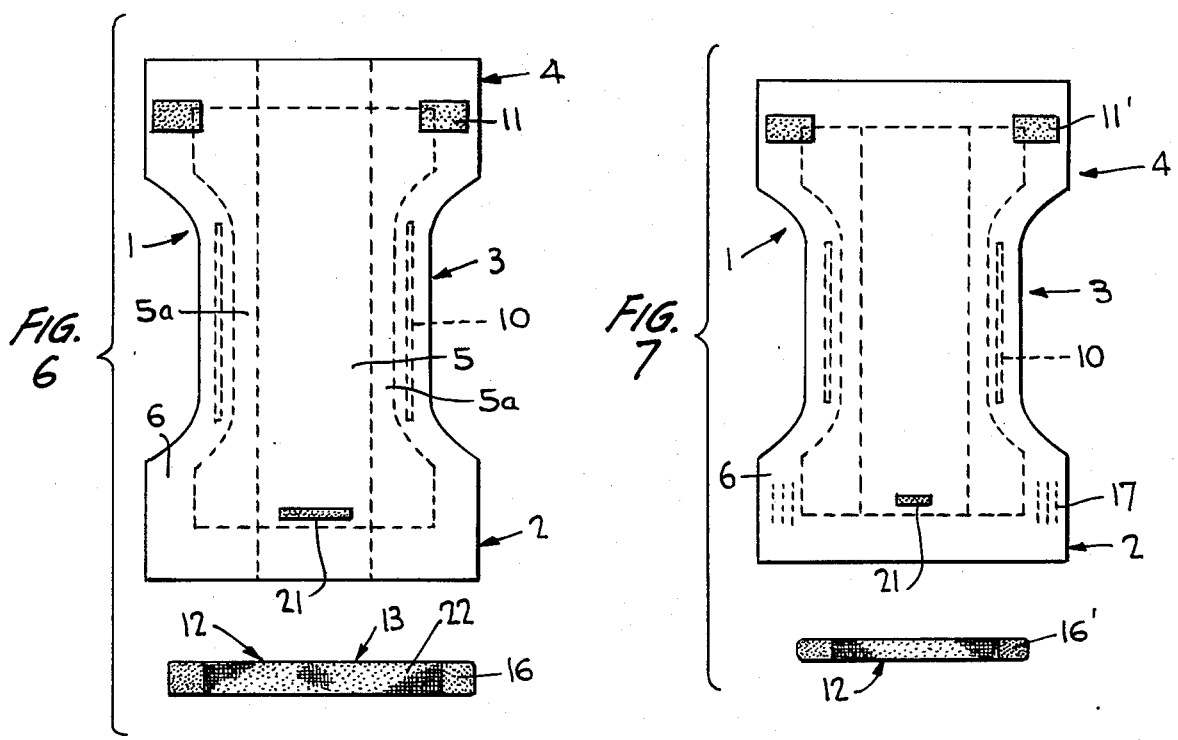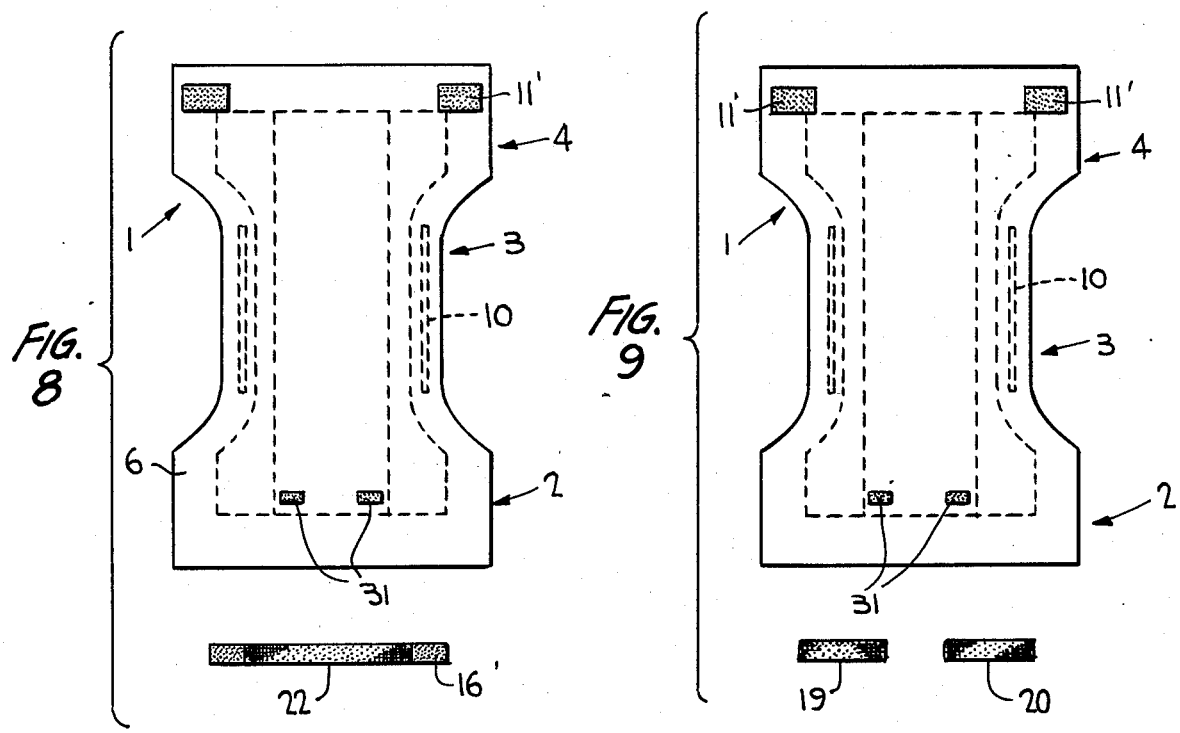

DISPOSABLE HYGIENIC ARTICLE WITH REMOVABLE BELT

The object of the invention is to provide a disposable hygienic article for absorbing liquids for babies and adults and more particularly it has as its aim to offer new means and an arrangement for maintaining said article against the user by means of a removable belt.

In general, such an article consists essentially of an absorbent pad consisting of a laminated structure comprising an absorbent cloth made of cellulose foam in which, if necessary, are incorporated powders absorbing several times their weight of liquid, covered on the face intended to be in contact with the skin of the user by a sheet permeable to liquids, at least in its central part, and on the opposite face, by a polyethylene film, the two sheets being partially or completely bonded to one another along their edges. In addition, means of attachment are provided in the truck areas in a manner such as to maintain the articles against the user.

The areas of the article that are intended, when in position, to be in contact with the abdomen and the back of the user are called "truck areas".

Among the many means of attachment offered (safety pins, buttons and button holes, hooks and eyes) adhesives and in particular pressure-sensitive adhesives are those that are most commonly used.

Adhesive attachment systems have the disadvantage, however, of not being "repositionable" once they have been placed in position, unless attachment means of complex structure are used, consisting of several superimposed layers as described in U.S. Pat. No. 3,951,149. The means of attachment are, on the one hand, very costly and, on the other, very difficult to produce on an industrial scale because of the various grades of adhesives which are required to be applied successively to various substrates.

In this application, the means of attachment are of the "buckle-grips" type, better known under the tradename of "Velcro" ®.

Many documents have already described disposable articles whose means of attachment consist of "Velcro" ® bands.

GB Pat. No. 1 428 572 describes a garment for babies, on the internal face of which is placed an absorbent pad, of which the edges of an external trunk area, folded over onto the other trunk area surrounding the baby's stomach, are maintained in position by means of "Velcro" ® bands, placed on the two trunk areas. A similar device is also described in U.S. Pat. Nos. 3,081,772 and 3,141,461 (FIG. 11).

U.S. Pat. No. 4,402,690 describes a device in which the edges of said internal trunk area are provided with a "Velcro" ® attachment means, while the edges of the other external trunk area are provided with complementary attachment means.

These articles, all of the multiple use type, described in these patents have the disadvantage of requiring the use of four "Velcro" ® elements of large size, two on the internal face, two on the external face. Such an arrangement, applied to single-use articles such as those which are the object of this invention would bear very heavily on the cost. For these elements are costly but it would nevertheless not be possible to limit their size too much, and in addition, the face of being obliged to removed the elements on the two faces complicates the production installations which would include a double element-positioning station, one for each side of the moving belt.

The same criticism could be made of the article described in U.S. Pat. No. 3,359,980. This article is provided with two "Velcro" ® bands, on the edges of the internal face of one trunk area and a complementary "Velcro" band over practically the whole of the width of the external face of the other trunk area.

In order to overcome these major disadvantages, it has been proposed to join the edges of the rear trunk areas of a nappy to those of the front areas located on the abdomen of the user, by means of two removable half-belts, fixed to one another by two complementary "Velcro" ® elements and to their respective edges by grip clips. This article is described in U.S. Pat. No. 4,158,906. In addition to the danger and discomfort which sharp edges can represent for a baby, and even an adult, this system has other great disadvantages. When the two jaws are fixed on each side to the rear areas of the article, the tensile stress exerted has a tendency to tear the edges of the nappy: the sheets covering the absorbent pad are thin, easily deformed or torn, properties which moreover, are guarantee of confort for the user. Thus the method of attachment proposed by this patent is usable only with great difficulty for disposable articles. In addition, the front part, which is not maintained in position has a tendency to slip.

PCT Patent No. 83/04163 reveals a nappy consisting of a front part provided with connecting points through which a fibrous material is passed, the rear part being provided with two half-lengths of fibrous material fixed to its rear opposite upper edge in a manner such as to maintain the nappy in position by passing two half-lengths through connecting points and tying the extremity of the fibrous materials around the abdomen of the user.

This nappy has certain disadvantages. For the connecting points particularly complicate the manufacture of the nappy. In addition, they limit the adjustment of the nappy on the user to a single position, or else other connecting points must be provided. In the case of a baby, the passage of fibrous materials through connecting points often require of the mother to use both hands, which is dangerous as a baby has a tendency to wriggle.

The interest of the invention which will be described hereinafter resides first in the method of attachment. Moreover, it provides very great saving from the economics point of view because the removable belt is reusable for several articles, in addition, it simplifies the industrial manufacture of the article.

According to the invention, the disposable article consists of:

(a) an absorbent pad of substantially rectangular shape comprising two trunk areas and a between-legs area, covered on its external face by a sheet impermeable to liquids, such as a sheet of polyethylene and on its internal face by a sheet permeable to liquids at least in the central area, these two sheets being partially or completely bonded to one another along their longitudinal edges, a first attachment element being fixed near each longitudinal edge on the external face of a trunk area.

(b) of a means of attachment associated removably, consisting of a belt provided at each end with a complementary second means of attachment of the first attachment element is characterized in that the other external area and/or at least one area of the belt coming into contact with this external trunk area is constituted in a manner such as to have a sufficient coefficient of friction such that when the article is in position it is maintained on the one hand, by the cooperation of the first attachment elements and, on the other, by the friction of one on the other of the trunk area and of said area of the belt.

In this specification, the terms "longitudinal" and "lateral" are defined with respect to the article without taking width or length into account. Thus, the edge which is part of the longitudinal edge of the article will be called "the longitudinal edge" of the rear area.

The term "internal" designates the faces which are directed towards the skin of the user. The user can be a baby or an adult suffering from incontinence. It has been found, however, that the article according to the invention is particularly advantageous for babies.

The sheet permeable to liquids at least in the central area can in particular be a non-woven sheet. It is also possible to place under this unwoven sheet two impermeable half-bands leaving a central opening, as wdescribed in Patent Application PCT No. 83/03051 of the Applicant Company.

The attachment elements located in the trunk area as well as at the extremities of the belt are of the buckle or grip type. This device is better known under the trade name of "Velcro" ®. But it is quite evident that the invention is not strictly limited to this type of element. It includes in general all the attachment elements which, when fixed, have a great resistance to shearing and a low resistance to peeling.

When the first attachment parts are "with buckles" the second attachment elements located at the extremities of the belt are with "grips". Similarly, when the first attachment elements are "with grips", the second are "with buckles". This last solution is preferred in the case of this invention.

These attachments are sized in a manner such as to allow the positioning to be adjusted and thus provide an excellent adaptation of the article to the user.

Of still greater preference, the first attachment elements are placed at a distance from the upper lateral edge of the trunk area in a manner such that said edge can be folded over towards the interior to improve the sealing around the waist circumference.

In order to provide better sealing of the article to be worn, two elastic strips are placed in the between-legs area, as described in French Pat. No. 2 011 778 of the Applicant Company and the first attachment elements are positioned outside and on both sides of the longitudinal area delimited by elastic strips (see their dummy extension) and the extreme lateral edges of the article.

The friction forces must be sufficiently great to prevent the belt slipping on the external face of the trunk area. This can be achieved in several ways:

The belt itself can have anti-slip properties. It is advantageously made of longitudinal fibrous materials including a part consisting of rubber threads, these latter preferably being combined by twisting.

Friction can also be obtained by an appropriate treatment with an antislip product of the external surface of the trunk area coming into contact with the belt and/or the belt area coming into contact with this trunk area. Of the anti-slip products that can be used, mention can be made of those which can be applied by coating. Coating can be continuous or in batches by areas or in lines. This second method is preferred. Anti-slip products can be applied in particular near the longitudinal edges of the belt and/or trunk area coming into contact with the belt. Another advantageous variant taken in combination or not in combination with the preceding consists in applying the anti-slip products to the belt along longitudinal lines.

Of the products permitting coating may be mentioned hot-setting adhesive with slight tack like acrylic emulsions. However, products that are not pressure-sensitive are preferred, hardening when cold, better known by the term "hot-melt".

Another means of obtaining high friction forces and improving the reciprocal holding in position of the belt and the external trunk area coming into contact with said belt consists in providing respectively complementary attachment elements.

In that case, the attachment element or elements located on the external trunk area in contact with the belt are identical with the attachment elements on the other trunk area. This has the advantage of enabling use to be made of a belt consisting of a band provided with complementary attachment elements over the whole of one face. It is preferable then that the attachment elements located on the belt be buckles, the attachment elements located on the trunk area being grips. In this way, the belt does not have any catching capability that could fix it to the garments of the baby. An advantageous embodiment consists in providing two attachment elements in the trunk area in contact with the belt and when these are located symmetrically with respect to the longitudinal axis of the nappy very efficient maintenance of the trunk area is obtained.

To improve still further this positioning maintenance, it is possible to treat the end facets of the trunk area in contact with the belt with an adhering coating having a low resistance to peeling or none, like thermosetting glues. It will be recalled that once a hygienic article has been placed in position on the body of a user, these end facets are covered with corresponding end facets of the other trunk area.

Preferentially, the belt is extendable so that the attachment of the trunk area in contact with the belt is still further improved. The maximum elongation of this belt is preferably greater than 30%. The belt can consist of a vinyl ethylene-acetate copolymer, but consists prefrably of extendable longitudinal fibrous materials enclosed in a rigid plastic grid. This structure confers on the belt very good longitudinal extensibility and practically no transversal extensibility. In addition, the protrusions formed by the fibrous materials with respect to the external polyethylene of the trunk area provide a high coefficient of friction.

The invention will be better understood by referring to the methods of embodiment illustrated by the drawings in the annex:

FIG. 1 is a plan view of the internal face of a nappy with the belt separate.

FIG. 2 is a transversal sectional view along AA of the nappy according to FIG. 1.

FIG. 3 is a perspective view of a nappy with the belt partially in position.

FIG. 4 is a perspective view of a nappy with the belt in position.

FIG. 5 is a perspective view of an apparatus on which the anti-slip treatment efficiency was tested.

FIGS. 6 to 9 represent the nappy according to four variants of the embodiment.

Nappy 1 is made according to the information in the French Patent application of the Applicant, No. 8 203 409. It is of substantially rectangular shape and comprises two trunk areas 2 and 4 and in between-legs area 3 whose edges have rounded or trapezoidal scalloping.

This nappy consists of an absorbent pad 5, made preferably of cellulose foam, if necessary charged with a "super absorbent" powder such as is described for example in U.S. Pat. No. 4,043,952.

The pad 5 is advantageously made of several successive layers leaving a central channel clear, as described in French patent application No. 8 317 723 and is enveloped in a soft tissue sheet 7. Its external face is covered with an impermeable sheet 6 such as of polyethylene and, on its internal face, partially covered by two impermeable semi-sheets 8, like polyethylene, cut out so as to form a central window 9 enabling urine to penetrate and themselves covered by a non-woven sheet 17. Between the two sheets 6 and 8 bonded to one another along their edges on both sides of the absorbent pad 5, in the between-legs area 3, are fixed, stretched, two elastic strips 10 enabling better sealing of the nappy to be obtained when it is in position.

In the rear area 4, on its external face, near the longitudinal edges and at a distance of about 5 cm from the upper lateral edge are positioned two "Velcro" ® attachment buckles made of polyamide. These two attachment elements 11 are located on both sides of the area delimited by the elastic laminated strips 10 (see their theoretical prolongation) and the extreme lateral edges of the article and are sufficiently wide (2 to 5 cm sides) to enable the positioning of the belt 12 to be adjusted, as described hereinafter.

Belt 12 is preferentially made of an elastic fabric band made of extendable longitudinal fibrous materials of LYCRA ® for example, 14 situated in a rigid strip 15 of plastic material such as polyamide.

At the extremities of belt 12 are fixed by means known in themselves two "Velcro" ® "grip" attachment elements 16 complementary to the "buckle" attachment elements 11.

When the nappy is placed in position, a first complementary attachment element 16 is fixed onto the attachment element 11, and the rear trunk area 4 is folded over in a manner such that the parts located near the longitudinal edges cover the edges of the other front trunk area 2. Then, the second complementary attachment element 16 is fixed onto the attachment element 11, remaining in a manner such that the belt is positioned on the abdomen of the user.

Another method of placing the article into position so that the belt is positioned on the flanks of the user can be envisaged.

The following figures are given as an indication of the dimensions (in cm) of a nappy for babies:
width of trunk areas: 31
length: 54
distance from first attachment elements to lateral upper edge: 5
distance of first attachment elements to longitudinal edge: 1
length of belt: 28
maximum elongation of belt: 67%

In accordance with the invention to obtain a high coefficient of friction between the contact surfaces antislip agents are incorporated in the material of the elements, for example rubber threads twisted in combination with the filaments of the belt or else at least one of these contact areas is treated.

The efficiency of the treatments applied to the belt is checked by means of an apparatus designed to simulate the forces which are exerted on the nappy in position and also, in vivo, on babies in creches.

The apparatus used to perform these tests is shown in FIG. 5.

A polyethylene sheet (100) is glued to a movable curved metal surface connected to a dynamometer. Two eccentric locking attachments maintain the elastic band (101) in contact with the polyethylene. The band is subjected to an elogation of 30% and 10 tractions are effected at a displacement speed of 150 mm/mn.

The following are measured:
the mean maximum force Fm (in newtons)—i.e. the limit maximum force beyond which the belt slips on the polyethylene sheet.

The maximum energy Em (in Joules) measured by integration. The energy value measured is very high as depending on whether when the belt begins to slip it "jumps" or on the contrary slides slowly, the energy expanded will be different. This method is therefore related to the coefficient of friction.

EXAMPLE 1

4 g/m of the hot-belt product "BERICOL 17 H 228" ® were deposited on the belt.

The deposit was obtained by spraying onto a polyamide strip along four longitudinal lines, symmetrically two by two with respect to the longitudinal axis of the belt and located near the longitudinal edges. The two external deposits were located at about 5 mm from the respective longitudinal edges.

After the product had hardened, two tests were performed according to the operating procedure described above:

The following results were obtained:
FM: 21.6 N
Em: 2.8 J

Tests performed on 60 babies weighing 12 to 18 kg each in a creche showed maintenance was perfect.

EXAMPLE 2

According to the operating procedure of Example 1, a same quantity of acrylic emulsion "ACRONAL 14D" ® was sprayed onto the belt.

The following results were obtained:
FM: 7.4 N
Em: 1.13 J

The creche tests revealed that maintenance in position, although quite acceptable, was less satisfactory than with the hot melt product.

EXAMPLE 3

1.2 g/m of the hot melt product Ferustick Ref. 73121Y ® made by the RMC Belix company was deposited linearly on the belt.

The deposit was applied by spraying, in strokes, on a strip of polyamide along four symmetrical longitudinal lines two by two with respect to the longitudinal axis of the belt located near the longitudinal edges. The two external deposits were located about 5 mm from the respective longitudinal edges.

After the product has hardened tests were performed in accordance with the operating procedure described above.

The following results are obtained:
Fm: 18.7 N
Em: 2.2 J

Tests performed on 60 babies weighing 2 to 8 kg each in a crech revealed that maintenance was perfect.

EXAMPLE 4

Before making the belt rubber threads were included in the LYCRA ® fibrous materials by twisting.

The following results are obtained:
Fm: 29.5 N
Em: 2.6 J

The creche tests revealed perfect maintenance of the belt.

FIGS. 6 to 9 relate to the methods of emmbodiment of the invention in which a high degree of friction is ensured by means of attachment of the same type as the first and second attachment elements.

In FIG. 6 the nappy is shown from the side of the external face, its elements similar to those in FIGS. 1 and 2 bear the same references. In this example pad 5 includes two lateral parts 5a which overlap onto the baby's thighs.

On the external area 2 is positioned a grip attachment element 21 along the axis of symmetry of the nappy and at the level of the part corresponding to the lateral extremity of the pad.

Belt 12 consists of a band of elastic fabric provided with buckle attachment elements 22 on one of its faces in area 13 coming into contact with the front area 2. At the extremities of the belt 12 are fixed by means known in themselves two grip attachment elements 16. Thus when the nappy is positioned on the baby, the fact that the belt itself consists of an attachment element enables the nappy to be safely and rapidly placed in position and maintained effectively in the front trunk area.

The nappy described in FIG. 7 is identical with the nappy described above except as regards the nature of the attachment elements:

the attachment elements 11' located in the rear trunk area 4 have grips whereas the attachment elements 16' located at the end of belt 12 are buckles. In this case the belt and the extremities consist of a single elastic band with buckles.

In addition, the end lateral facets of the front trunk area 2 are treated along the line 17 with a glue having a low resistance to peeling like hot melt glues in a manner such as to still further improve maintenance of the front trunk area when the nappy is placed into position.

The nappy shown in FIG. 8 is identical with the nappy described in FIG. 7 except as regards the number of attachment elements:

Instead of a single attachment element located in the front area at the centre, two analogous attachment elements 31 are provided but located at the same level with respect to the absorbent pad on both sides of the longitudinal axis of the nappy, still in the median part of the pad: this arrangement still further improves the stability of the front trunk area.

When the nappy is placed into position, one of the extremities 16' of belt 12 is fixed on an attachment element 11', the front area is then folded over so that belt 12 is fixed on the other attachment element 11' and on the two attachment elements 31.

The nappy shown in FIG. 9 is a variant of that shown in FIG. 8 as regards structure of the belt.

This latter consists of two identical elements 19, 20 cut from an elastic band with buckles. When the nappy is placed into position the extremities of the half-belt 19 are fixed onto the attachment elements 11', 31 located on the same side of the nappy and the extremities of the half-belt 20 are fixed onto the attachment elements 11',31 located on the other side of the belt.

What is claimed is:

1. A disposable hygienic article (1) consisting:
   (a) of an absorbent pad (5) of substantially rectangular shape comprising two trunk areas (2) and (4) and a between-legs area (3) covered on its external face by a sheet (6) impermeable to liquids, such as a sheet of polyethylene, and on its internal face by a sheet (8) permeable to liquids at least in the central area (9), these two sheets being partially or completely bonded to one another along their longitudinal edges, a first attachment element (11, 11') being fixed near each longitudinal edge on the external face of a trunk area (4)
   (b) and a means of attachment associated removably, consisting of a belt (12) provided at each end with a complementary second means of attachment (16, 16') of the first attachment element (11, 11') characterized in that the other external area (4) and/or at least one area (13) of the belt coming into contact with this external trunk area is constituted in a manner such as to have a sufficient coefficient of friction such that when the article is in position it is maintained on the one hand by the cooperation of the first attachment elements and, on the other, by the friction of one on the other of the trunk area (4) and of said belt area (13).

2. Article according to claim 1 characterized in that the first attachment elements (11) located on the external face of the trunk area (4) are with "buckles" and the second attachments elements (16) with "grips" type.

3. A disposable article according to any of the preceding claims, characterized in that the attachment elements (11, 11') are located at a distance from the upper lateral edge of the trunk area (4) such that when in position it can be folded inwards to improve the sealing around the waist.

4. A disposable article according to one of the preceding claims, characterized in that on both sides the absorbent pad (5) in the between-legs area (3) are fixed to elastic laminated strips (10) and in that the first attachment elements (11, 11') are positioned outside the area delimited by the elastic laminated strips (10)—see their theoretical extension—and the extreme lateral edges of the article.

5. A disposable article according to one of the preceding claims, characterized in that belt (12) is extendable.

6. A disposable article according to one of the preceding claims, characterized in that belt (12) is formed of longitudinal fibrous materials (14) with which are combined rubber threads, for example by twisting.

7. A disposable article according to claim 6, characterized in that the longitudinal fibrous materials are enclosed in a rigid plastic grid (15).

8. A dispposable hygienic article according to one of the claims 1 to 5, characterized in that the external trunk area coming into contact with the belt and/or area (13) of the belt coming into contact with this trunk area is treated at least partially with an anti-slip product.

9. An article according to claim 8 characterized in that the anti-slip product is deposited by coating.

10. An article according to claim 9 characterized in that the anti-slip product is not pressure-sensitive, heat meltable and cold hardenable.

11. An article according to one of the claims 9 or 10, characterized in that coating is discontinuous by areas or lines.

12. An article according to one of claims 9 to 11, characterized in that the anti-slip product is deposited near the longitudinal edges of the belt and/or the external trunk area coming into conact with the belt.

13. An article according to claim 1, characterized in that the anti-slip product is based on rubbr threads.

14. A disposable article according to one of the claims 8 to 12, characterized in that the anti-slip product is deposited along longitudinal lines on the belt.

15. A disposable article according to claim 14, characterized in that the anti-slip product is extendable.

16. A disposable hygienic article according to one of the claims 1 to 5, characterized in that area (13) of the belt in contact with the external trunk area is provided with at least one attachment element (22) and in that said external trunk area (2) is provided with at least one complementary attachment element (21) of said element (22).

17. A hygienic article according to claim 16, characterized in that the attachment element or elements (21) are identical with the attachment elements (11, 11') located in the other trunk area (4).

18. A hygienic article according to one of the claims 16 or 17, chracterized in that the attachment element or elements on the belt are buckles.

19. A hygienic article according to one of the claims 16 to 18, characterized in that two attachment elements (31) are present in the trunk area (2) in contact with the belt.

20. A hygienic article according to claim 19, characterized in that the attachment elements (31) are present on both sides and symmetrically with respect to the longitudinal axis of the nappy.

21. A hygienic article according to claims 16, 19 and 20, characterized in that the belt (12) consists of two identical elements (19,20).

22. A hygienic article according to one of the preceding claims characterized in that the lateral facets of the trunk area 2 in contact with the belt are treated with an adherent coating having no or very slight resistance to peeling.

* * * * *